(12) United States Patent
Bryning et al.

(10) Patent No.: US 7,704,363 B2
(45) Date of Patent: Apr. 27, 2010

(54) METHODS AND APPARATUS FOR THE LOCATION AND CONCENTRATION OF POLAR ANALYTES USING AN ALTERNATING ELECTRIC FIELD

(75) Inventors: Zbigniew T. Bryning, Campbell, CA (US); Theresa B. Taylor, Sunnyvale, CA (US)

(73) Assignee: Applied Biosystems, LLC, Foster City, CA (US)

( * ) Notice: Subject to any disclaimer, the term of this patent is extended or adjusted under 35 U.S.C. 154(b) by 1124 days.

(21) Appl. No.: 11/288,664

(22) Filed: Nov. 28, 2005

(65) Prior Publication Data

US 2006/0081474 A1    Apr. 20, 2006

Related U.S. Application Data

(63) Continuation of application No. 10/281,770, filed on Oct. 27, 2002, now Pat. No. 6,969,454, which is a continuation of application No. 09/522,638, filed on Mar. 10, 2000, now Pat. No. 6,537,433.

(51) Int. Cl.
*G01N 27/447*    (2006.01)
*G01N 27/453*    (2006.01)

(52) U.S. Cl. .................. 204/547; 204/643; 204/600; 204/450

(58) Field of Classification Search ............ 204/450, 204/600, 547, 643
See application file for complete search history.

(56) References Cited

U.S. PATENT DOCUMENTS

| 4,874,507 | A | 10/1989 | Whitlock |
| 4,911,806 | A | 3/1990 | Hofmann |
| 4,956,065 | A | 9/1990 | Kaler et al. |
| 5,059,294 | A | 10/1991 | Lizardi |
| 5,275,710 | A | 1/1994 | Gombocz et al. |
| 5,344,535 | A | 9/1994 | Betts et al. |
| 5,454,472 | A | 10/1995 | Benecke et al. |
| 5,489,506 | A | 2/1996 | Crane |
| 5,569,367 | A | 10/1996 | Betts et al. |
| 5,569,591 | A | 10/1996 | Kell et al. |
| 5,572,076 | A | 11/1996 | Benecke et al. |
| 5,589,047 | A | 12/1996 | Coster et al. |
| 5,605,662 | A | 2/1997 | Heller et al. |

(Continued)

FOREIGN PATENT DOCUMENTS

DE    19500683 A1    6/1996

(Continued)

OTHER PUBLICATIONS

Ajdari et al., "Free-flow Electrophoresis with Trapping by a Transverse Inhomogeneous Field," *Proc. Natl. Acad. Sci. USA*, 88:4468-4471 (1991).

(Continued)

*Primary Examiner*—Alex Noguerola (57) ABSTRACT

A method is disclosed for effecting the concentration of a polar analyte in an alternating electric field. In the method, a relative translation of the polar analyte and an alternating electric field along a translation path is effected. A portion of the polar analyte is then trapped and concentrated in a concentration zone formed by the intersection of the translation path and the alternating electric field. Also disclosed are various devices for carrying out the forgoing method.

27 Claims, 7 Drawing Sheets

U.S. PATENT DOCUMENTS

| | | | |
|---|---|---|---|
| 5,626,734 | A | 5/1997 | Docoslis et al. |
| 5,632,957 | A | 5/1997 | Heller et al. |
| 5,667,654 | A | 9/1997 | Gombocz et al. |
| 5,746,934 | A | 5/1998 | Sasaki et al. |
| 5,869,004 | A | 2/1999 | Parce et al. |
| 5,948,231 | A | 9/1999 | Fuchs et al. |
| 5,948,328 | A | 9/1999 | Fiedler et al. |
| 6,007,690 | A | 12/1999 | Nelson et al. |
| 6,056,861 | A | 5/2000 | Fuhr et al. |
| 6,149,789 | A | 11/2000 | Benecke et al. |
| 6,185,084 | B1 | 2/2001 | Tai et al. |
| 6,203,683 | B1 | 3/2001 | Austin et al. |
| 6,218,126 | B1 | 4/2001 | Yasuda et al. |
| 6,280,590 | B1 | 8/2001 | Cheng et al. |
| 6,310,309 | B1 | 10/2001 | Ager et al. |
| 6,352,838 | B1 | 3/2002 | Krulevitch et al. |
| 6,432,630 | B1 | 8/2002 | Blankenstein |
| 6,448,794 | B1 | 9/2002 | Cheng et al. |
| 6,465,225 | B1 | 10/2002 | Fuhr et al. |
| 6,537,433 | B1 | 3/2003 | Bryning et al. |
| 6,572,830 | B1 | 6/2003 | Burdon et al. |
| 6,596,143 | B1 | 7/2003 | Wang et al. |
| 6,605,453 | B2 | 8/2003 | Ozkan et al. |
| 6,610,188 | B1 | 8/2003 | Fuhr et al. |
| 6,660,493 | B2 | 12/2003 | Miles |
| 6,663,757 | B1 | 12/2003 | Fuhr et al. |
| 6,673,225 | B1 | 1/2004 | Arnold |
| 6,685,812 | B2 | 2/2004 | Miles |
| 6,706,163 | B2 | 3/2004 | Seul et al. |
| 6,716,620 | B2 | 4/2004 | Bashir et al. |
| 6,727,451 | B1 | 4/2004 | Fuhr et al. |
| 6,730,204 | B2 | 5/2004 | Mariella, Jr. |
| 6,744,038 | B2 | 6/2004 | Wang et al. |
| 6,761,811 | B2 | 7/2004 | Mariella, Jr. |
| 6,764,583 | B2 | 7/2004 | Miles |
| 6,780,584 | B1 | 8/2004 | Edman et al. |
| 6,784,420 | B2 | 8/2004 | Wang et al. |
| 6,787,018 | B1 | 9/2004 | Miles et al. |
| 6,815,664 | B2 | 11/2004 | Wang et al. |
| 6,824,664 | B1 | 11/2004 | Austin et al. |
| 6,833,542 | B2 | 12/2004 | Wang et al. |
| 6,858,184 | B2 | 2/2005 | Pelrine et al. |
| 6,875,329 | B2 | 4/2005 | Washizu et al. |
| 6,881,314 | B1 | 4/2005 | Wang et al. |
| 6,887,362 | B2 | 5/2005 | Huang et al. |
| 6,936,811 | B2 | 8/2005 | Kibar |
| 6,942,776 | B2 | 9/2005 | Medoro |
| 6,949,176 | B2 | 9/2005 | Vacca et al. |

FOREIGN PATENT DOCUMENTS

| | | | |
|---|---|---|---|
| EP | 1335198 | B1 | 8/2003 |
| GB | 2266153 | A | 10/1993 |
| WO | WO 93/05390 | A1 | 3/1993 |
| WO | WO 96/42013 | A1 | 12/1996 |
| WO | WO 97/27933 | A1 | 8/1997 |
| WO | 99/63332 | A1 | 12/1999 |
| WO | WO 99/62622 | A1 | 12/1999 |
| WO | WO 00/73780 | A1 | 12/2000 |

OTHER PUBLICATIONS

Allsopp et al., "Coupling of Dielectrophoresis with Capillary Electrophoresis for Microbiological Application," *Electronic Devices and Circuits Research Projects*, 2000 http://www.york.ac.uk/dept/elec/resrev/sub4/sub412.htm.

Asbury et al., "Trapping of DNA in Nonuniform Oscillating Electric Fields," *Biophysical Journal*, 74:1024-1030 (1998).

Asbury et al., "Manipulation of Single DNA Molecules by Induced-Dipole Forces in Micro-Fabricated Structures," *Dept. of Molecular Biotechnology*, University of Washington, Abstract, Feb. 5, 1999.

Bakewell, D. et al., "Characterisation of the Dielectrophoretic Movement of DNA in Micro-Fabricated Structures," *Inst. Phys. Conf.* Ser. No. 163, paper presented at the $10^{th}$ Int. Conf., Cambridge, pp. 73-76 (Mar. 28-31, 1999).

Buck et al., "Localized, Positive Charge Mediates Adhesion of *Rhodosporidium toruloides* to Barley Leaves and Polystyrene," *Applied and Environmental Microbiology*, May 1999, p. 2179-2183.

Cheng, Jing et al., "Preparation and Hybridization Analysis of DNA/RNA from *E. coli* on Microfabricated Bioelectronic Chips," *Nature Biotechnology*, 16:541-546 (1998).

Chou, Chia-Fu et al., "DNA Trapping by Electrodeless Dielectrophoresis," A13.003 *Abstract Submitted for the Mar00 Meeting of the American Physical Society*, submitted Dec. 3, 1999.

Dai et al., "Surface Water Quality—Evaluation of Attachment of *Cryptosporidium parvum* and *Giardia Lamblia* to Soil Particles," *J. Environ. Qual.*, 32:296-304 (2003).

Fuhr, Gunter et al., "Particle Micromanipulator Consisting of Two Orthogonal Channels with Traveling-Wave Electrode Structures," *Sensor and Actuators A* 41-42:230-239 (1994).

Fuhr, Gunter et al., "Positioning and Manipulation of Cells and Microparticles Using Miniaturized Electric Field Traps and Travelling Waves," *Sensors and Materials*, Scientific Publishing Division of My, Tokyo, Japan 7(2):131-146 (1995).

Garcia, Manual and Clague, David, "The 2D Electric Field Above a Planar Sequence of Independent Strip Electrodes," *J. Phys. D.: Appl. Phys.* 33:1747-1755 (2000).

Goater, A.D. et al., "Single *Cryptosporidium oocyst* Isolation and Capture Using a Travelling-Wave Dielectrophoresis Device," *Inst. Phys. Conf.* Ser. No. 163, pp. 69-72, paper presented at the $10^{th}$ Int. Conf., Cambridge (Mar. 28-31, 1999).

Heida et al., "Trapping Neurons by Dielectrophoretic Forces," Abstract, Jan. 13, 1999, http://www.nmi.de/meameeting/abstracts/heida.htm.

Heller, et al., "Control of Electrohydrodynamic Distortion of Sample Streams in Continuous Flow Electrophoresis Using Oscillating Fields," *Electrophoresis*, 14(12):1278-1283 (1993).

Huang, Ying et al., "Electric Manipulation of Bioparticles and Macromolecules on Microfabricated Electrodes," *Anal. Chem.* 73(7):1549-1559 (2001).

Kricka, Larry J., "Revolution on a Square Centimeter," *Nature Biotechnology*, 16:513-514 (1998).

Lumpkin, O., "Length Dependent Mobility of Large DNAs in Oscillating Crossed Electric and Magnetic Fields," *J. Chem. Phys.*, 92(6):3848-3852 (1990).

Milner, K.R. et al., "Analysis of Biological Particles Using Dielectrophoresis and Impedance Measurement," *Biomedical Sciences Instrumentation*, 34:157-162.

Mizuno, Akira et al., "Handling of a Single DNA Molecule Using Electric Field and Laser Beam," *IEEE Transactions on Industry Applications*, 31(6):1452-1457 (1995).

Morgan, Hywel et al., "Separation of Submicron Bioparticles by Dielectrophoresis," *Biophysical Journal* 77:516-525 (1999).

Morishima et al., "Design of a Microchannel for Capillary Electrophoresis in Combination with Dielectrophoresis," *Dept. of Chemistry*, Stanford University, CA25.

Pethig, R. et al., "Development of Biofactory-on-a-chip Technology Using Excimer Laser Micromachining," *J. Micromech. Microeng.* 8:57-63 (1998).

Taylor et al., "Process Control for Optimal PCR Performance in Glass Microstructures," *Journal of Biomedical Microdevices*, 1(1):65-70 (1998).

Tomlinson et al., "Enhancement of Concentration Limits of Detection in CE and CE-MS: A Review of On-line Sample Extraction, Cleanup, Analyte, Preconcentration, and Microreactor Technology," *J. Cap. Elec.*, 002, 6:247-266.

Wang Xiao-Bo et al., "Dielectrophoretic Manipulation of Particles," *IEEE Transactions on Industry Applications*, 33(3):660-669 (1997).

Washizu et al., "Electrostatic Manipulation of DNA in Microfabricated Structures," *IEEE Transactions on Industry Applications*, 26(6):1165-1172 (1990).

Washizu et al., "Molecular Dielectrophoresis of Biopolymers," *IEEE Transactions on Industry Applications*, 30(4):835-843.

Washizu et al., "Applications of Electrostatic Stretch-and-Positioning of DNA," *IEEE Transactions on Industry Applications*, 31(3):447-456 (1995).

U.S. Appl. No. 60/128,127.

Abstract of Cerbon et al., "Surface Potential Regulation of Phospholipid Composition and in-out Translocation in Yeast," *European Journal of Biochemistry*, vol. 219, 195-200 (1994).

Heida et al., "Trapping Neurons by Dielectrophoretic Forces," Abstract, Jan. 13, 1999, http://www.nmi.de/meameeting/ abstracts/heida.htm.

METHODS AND APPARATUS FOR THE LOCATION AND CONCENTRATION OF POLAR ANALYTES USING AN ALTERNATING ELECTRIC FIELD

FIELD OF THE INVENTION

This invention relates to methods and apparatus for the location and concentration of polar analytes using an alternating electric field.

BACKGROUND

A recent trend in the field of analytical instrumentation has been the development of integrated microfluidic devices in which multiple operations are performed on a single device, e.g., Harrison et al., "Micromachining a Miniaturized Capillary Electrophoresis-Based Chemical Analysis System on a Chip," *Science*, 261: 895 (1992). Such devices offer many advantages over conventional analytical formats including the ability to handle very small volumes; ease and economy of device fabrication; the ability to integrate multiple operations onto a single integrated device; and the opportunity to achieve a high degree of automation.

In many chemical and biochemical analysis methods performed using microfluidic devices, it is advantageous to concentrate an analyte as part of the analysis. For example, increased analyte concentration generally leads to increased chemical reaction rates, increased rates of mass transfer, and enhanced detectability. However, because conventional concentration methods require a solid phase pullout step (e.g., adsorption), or a phase change of the analyte (e.g., precipitation), or a phase change of the solvent (e.g., evaporation), these methods are not well adapted for use in a microfluidic device.

In addition, methods for controlling the location of an analyte are important in the design of methods using microfluidic devices. For example, prior to a separation step, it may be desirable to locate a sample volume in a spatially-defined injection zone.

Therefore, it would be desirable to have a method for the location and concentration of an analyte that is well suited for use in integrated microfluidic systems.

SUMMARY

The present invention is directed towards our discovery of methods and devices for the location and concentration of polar analytes using an alternating electric field.

In a first aspect, the present invention provides a method for the concentration of a polar analyte comprising the steps of effecting the relative translation of the polar analyte and an alternating electric field along a translation path such that a portion of the polar analyte is trapped and concentrated in a concentration zone formed by the intersection of the translation path and the alternating electric field.

In a second aspect, the present invention provides a device for the concentration of a polar analyte comprising a translation path, a first set of electrodes located to provide a first electric field effective to cause the electrokinetic translation of a polar analyte along the translation path, and a second set of electrodes located to provide an alternating second electric field intersecting the translation path and sufficient to trap and concentrate a portion of the polar analyte in a concentration zone formed by the intersection of the translation path and the alternating second electric field.

It is a first object of the invention to provide a method for the concentration of a polar analyte that does not require a solid-phase pull-out step or a phase change of the polar analyte or a solvent.

It is a second object of the invention to provide a method for the manipulation or location of a polar analyte that does not require a solid-phase pull-out step or a phase change of the polar analyte or a solvent.

It is a third object of the invention to provide a method for the concentration or manipulation of a polar analyte that does not require manual intervention and is therefore well suited to automation.

It is a fourth object of the invention to provide a method for the concentration or manipulation of a polar analyte that is well suited for use in a microfluidic device.

The present invention will become better understood with reference to the following written description, drawings, and appended claims.

DETAILED DESCRIPTION OF THE PREFERRED EMBODIMENTS

Reference will now be made in detail to certain preferred embodiments of the present invention, examples of which are illustrated in the accompanying drawings. While the invention will be described in conjunction with selected preferred embodiments, it will be understood that these embodiments are not intended to in any way limit the scope of the invention. On the contrary, the invention is intended to cover alternatives, modifications, and equivalents, which may be included within the scope of the invention as determined by the appended claims. In addition, as used in this disclosure, the plural and singular numbers will each be deemed to include the other; "or" is not exclusive; and "includes" and "including" are not limiting.

Generally, the present invention comprises methods and apparatus for locating and concentrating a polar analyte at a specified location by effecting the relative translation of the polar analyte with respect to an alternating electric field along a translation path such that the polar analyte is concentrated in a concentration zone formed by the intersection of the translation path and the alternating electric field.

The invention is based in part on the discovery that when a polar analyte passes into an alternating electric field having the appropriate characteristics, the polar analyte will become trapped in a concentration zone formed by the alternating electric field. While the theoretical explanation for this highly unexpected and beneficial phenomena is not well understood, and the present invention is not intended to be limited in any way by the following or any other theoretical explanation, it is thought by the inventors that this trapping phenomenon is related to the Winslow effect, also referred to as the electrorheological effect, in which polar entities align themselves head-to-tail along the field lines of an electric field thereby forming filamentous structures, e.g., Winslow, *J. Applied Physics* (1947); and Winslow, U.S. Pat. No. 2,417,850.

I. DEFINITIONS

Unless stated otherwise, the following terms and phrases as used herein are intended to have the following meanings:

"Translation path" means a path described as a result of a relative translation of an alternating electric field and a medium potentially containing a polar analyte. The translation path may have any shape, e.g., straight, curved, and the like.

"Separation channel" means a channel used to conduct a separation process, e.g., separations based on electrokinetic, chromatographic, or other like process.

"Electrokinetic translation" means the movement of an entity in response to an electric field. Exemplary electrokinetic translation processes include but are not limited to electrophoresis, dielectrophoresis, electroendoosmosis, micellar electrokinetic chromatography, isotachophoresis, and combinations of the foregoing processes.

"Electrokinetic translation system" means an apparatus effective to cause the electrokinetic translation of a polar analyte. Typically, an electrokinetic translation system will include a channel for supporting a medium, a power supply, a set of two or more electrodes in electrical communication with the channel, and electrical connections between the power supply and the two or more electrodes.

"Dipole moment" means the product q*R where q and –q are charges of opposite polarity that are separated by a distance R. As used in the following discussion, a dipole moment includes a permanent dipole moment, a dipole moment resulting from the electric-field-induced polarization of an entity having a finite polarizability, a dipole moment resulting from the orientation of an entity, e.g., orientation polarization, a dipole moment resulting from the electric-field-induced space-charge distortion of a counter-ion atmosphere surrounding an entity e.g., a Debye layer, or a dipole moment resulting from any combination of the foregoing mechanisms.

"Alternating electric field" means an electric field characterized by a vector whose magnitude or direction varies with time. Included within the definition of an alternating electric field is a multi-phase electric field. The limits of the spatial extent of an alternating electric field is that region in which the electric field strength of the alternating electric field is greater than that required to trap and concentrate a polar analyte of interest with respect to the alternating electric field.

"Polar analyte" means an analyte having a dipole moment.

II. METHODS

Figure 1:
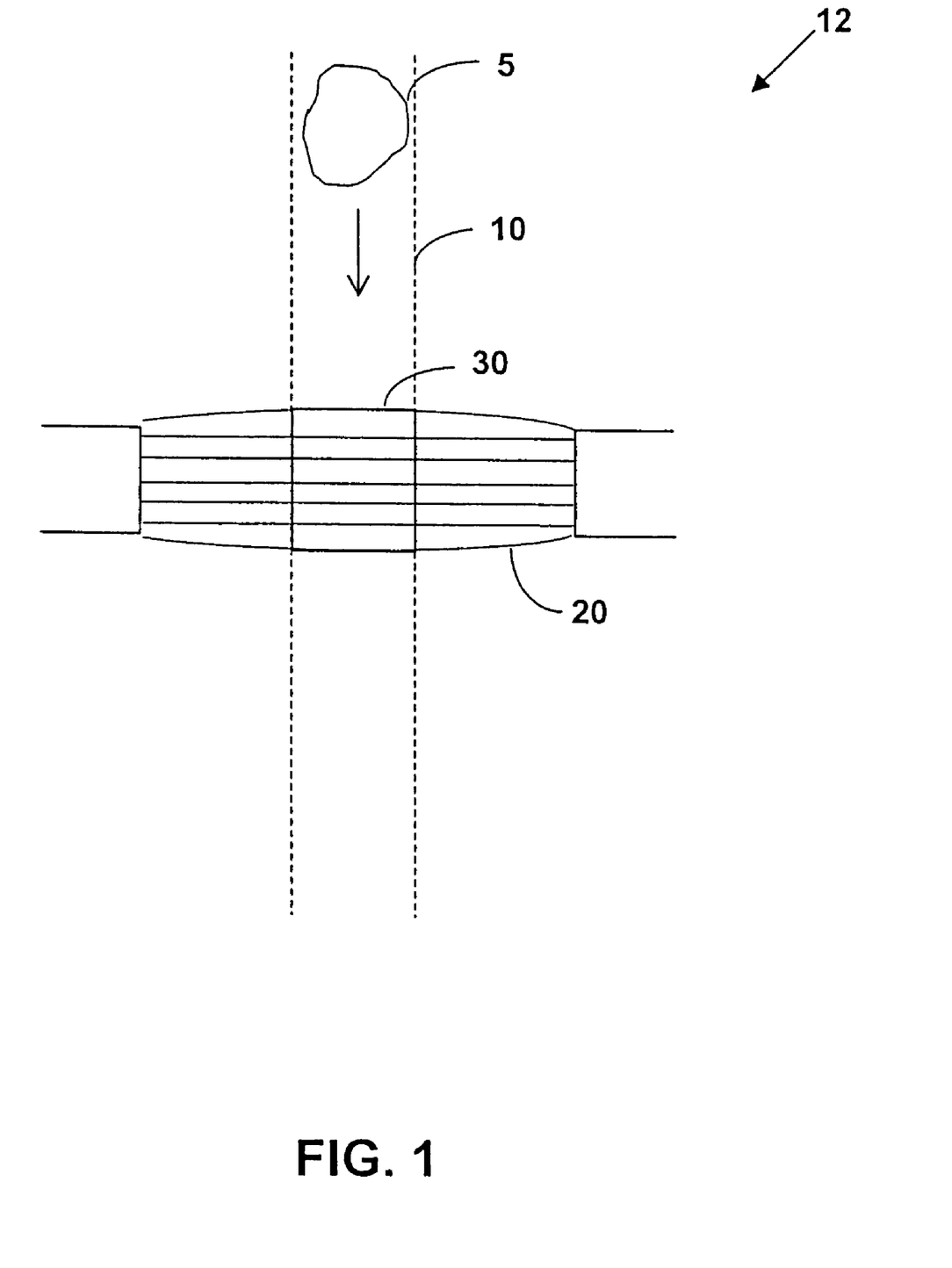
FIG. 1 is a schematic representation of a preferred method according to the present invention.

Referring to FIG. 1, in a preferred embodiment, the method of the invention comprises a method for the location and concentration of a polar analyte 5 comprising the steps of effecting the relative translation of the polar analyte 5 along a translation path 10, and effecting an alternating electric field 20 which intersects the translation path 10 such that some or all of the polar analyte 5 is trapped and concentrated in a concentration zone 30 formed by the intersection of the translation path 10 and the alternating electric field 20.

The polar analyte 5 for use in the methods of the present invention may be any analyte having a dipole moment. The polar analyte may be charged or uncharged, and if the polar analyte is charged, it may have an overall net charge or be neutral. Preferably, to the polar analyte will be present in a buffered electrolyte solution, more preferably an electrolyte solution having a low ionic strength. Exemplary polar analytes include nucleic acids, both single and double stranded, proteins, carbohydrates, viruses, cells, organelles, organic polymers, particles, and the like. A particularly preferred polar analyte for use in the methods of the present invention is single or double stranded nucleic acid dissolved in an electrolyte.

The means used to effect the relative translation of the polar analyte 5 with respect to the alternating electric field 20 along the translation path 10 may be any of a number of different means, or combinations of means, capable of causing the polar analyte to become located in a concentration zone 30. Such relative translation may be effected by movement of the polar analyte 5, movement of the alternating electric field 20, or by movement of both the polar analyte 5 and the alternating electric field 20.

For example, the means used to effect the relative translation of the polar analyte with respect to the alternating electric field may be simple gravity forces. Alternatively, translation of the polar analyte 5 may be induced by spinning the system 12 about a selected axis so as to impose a centrifugal force having a component directed along the translation path 10. Instead, the polar analyte 5 may be caused to move along the translation path 10 by capillary action or other surface-mediate processes. Alternatively, active hydraulic pumping may be employed to move the polar analyte 5 along the translation path as a result of a pressure gradient, e.g., using a conventional microvolume syringe pump. In yet another preferred embodiment where the polar analyte is magnetic, a magnetic field may be used to cause the translation of the polar analyte along the translation path, e.g., using a permanent magnet or an electromagnet. In an additional preferred embodiment of the subject invention, an electric field may be used to effect the translation of the polar analyte by an electrokinetic translation processes.

Where the means for effecting the relative translation of the polar analyte with respect to the alternating electric field is effected by movement of the alternating electric field 20, such movement may be achieved by mounting the electrodes used to form the alternating electric field on a moveable stage connected to a conventional mechanical translation system. The mechanical translation system may effect the linear or non-linear translation of the electrodes. Such mechanical translation systems are well known in the art, e.g., Hunkapiller et al., U.S. Pat. No. 4,811,218; and Hueton et al., U.S. Pat. No. 5,459,325. Exemplary mechanical translation systems include electromechanical systems, e.g., a lead screw or belt drive connected to a motor, piezoelectric actuators, or pneumatic or hydraulic systems, e.g., a piston-in-cylinder drive system. One particularly preferred mechanical translation system comprises a computer-controlled-DC-servo-motor-driven XY translation stage.

Regardless of the means used to effect the relative translation of the polar analyte with respect to the alternating electric field along the translation path, during the concentration process, the forces used to effect the relative translation must not be so strong so as to overwhelm the trapping forces of the alternating electric field. Rather, the forces used to cause the relative translation along the translation path should be balanced against the trapping forces used to trap the polar analyte in the concentration zone as discussed in more detail below.

The alternating electric field 20 used to trap the polar analyte can be any alternating electric field effective to trap and concentrate a polar analyte. Generally, the alternating electric field of the invention may be characterized by a time vs. field strength profile, a frequency, and a maximum field strength. The properties of the alternating electric field required to trap the polar analyte will depend on a number of easily accessible experimental parameters including the magnitude of the dipole moment of the polar analyte, the dielectric constant of the supporting medium, and, in the case of a polar analyte having an induced dipole moment, the polarizability of the polar analyte or surrounding counterion atmosphere.

The time vs. field strength profile of the alternating electric field may be sinusoidal, sawtooth, rectangular, superpositions of the foregoing, periodic or non-periodic, or any other profile capable of being generated using a modern function generator, e.g., a Model 33120A 15 MHz Function/Arbitrary Waveform Generator from Agilent Technologies. Preferably, the time vs. field strength profile of the alternating electric field is rectangular. The rectangular profile is preferred because it has essentially no zero-field component, resulting in a high effective duty cycle. In a particularly preferred embodiment, the time vs. field strength profile of the alternating electric field is such that the time-averaged integrated field strength is zero where the average is taken over one complete cycle. This profile is preferred because it minimizes the extent to which a polar analyte located in the concentration zone will be translated within the concentration zone in a direction other than along the translation path, and it reduces the amount of electrochemical reaction products produced at the surface of the electrodes, e.g., gas bubbles.

The frequency of the alternating electric field may be any frequency capable of trapping a portion of a polar analyte. However, for many polar analytes of practical importance, the frequency of the alternating electric field is preferably between about 10 Hz and 100 megahertz (MHz), and more preferably between about 1 kilohertz (KHz) and 100 KHz.

While the maximum field strength of the alternating electric field may be any field strength suitable to a particular application, preferably, the maximum field strength of the alternating electric field, as measured by the peak field strength of the alternating electric field, is between about 100 V/cm and 10,000 V/cm, and more preferably between about 1,000 V/cm and 20,000 V/cm.

The alternating electric field may be spatially uniform or spatially non-uniform. For example, the alternating electric field may be used to effect dielectrophoretic transport.

A trapped polar analyte may be released from a concentration zone by either reducing the trapping strength of the alternating electric field or by increasing the force used to effect the relative translation of the polar analyte with respect to the alternating electric field. The trapping strength of the alternating electric field may be modulated by changing the frequency, field strength, or both. Alternatively, the polar analyte can be released from the concentration zone by increasing the forces used to effect the relative translation of the polar analyte and the alternating electric field, e.g., by increasing the electric field used to drive electrokinetic translation of the polar analyte, increasing the pressure used to drive a pressure-driven flow of the polar analyte, or increasing the rate of translation of the alternating electric field.

In a preferred embodiment, subsequent to an analyte concentration step according to the methods of the present invention, a further analytical step is performed. In one preferred embodiment, after a polar analyte has been concentrated in a concentration zone, the polar analyte is directed into an analytical separation process, for example an electrokinetic or chromatographic separation process. The concentration and localization methods of the present invention are particularly advantageous where the subsequent analytical separation process is electrophoresis because the pre-separation concentration step can provide a concentrated and narrow injection zone leading to both increased separation performance, e.g., decreased plate height, and enhanced detectability of the separated components.

In a preferred embodiment of the present invention in which the polar analyte is a nucleic acid, subsequent to or during the concentration of the analyte nucleic acid in the concentration zone, the nucleic acid analyte is subjected to a nucleic acid hybridization reaction in which the concentrated nucleic acid analyte is contacted with one or more complementary nucleic acids under conditions suitable for sequence-specific hybridization. In a particularly preferred embodiment, the complementary nucleic acids are bound to a solid support, e.g., an array of support-bound nucleic acids including one or more potentially complementary nucleic acids. The support-bound nucleic acids may be synthetic polynucleotide probes, cDNA molecules, or any other nucleic acid or nucleic acid analog capable of sequence-specific hybridization. Exemplary arrays of support-bound nucleic acids are described elsewhere, e.g., Singh-Gasson et al., *Nature Biotechnology*, 17: 974-978 (1999); Blanchard and Friend, *Nature Biotechnology*, 17: 953 (1999); Brown et al., U.S. Pat. No. 5,807,522. The pre-hybridization concentration step of the present invention may result in an increased rate of hybridization, the ability to use a less concentrated sample, or an enhancement of the detectability of the products of the hybridization reaction. While this embodiment has been described in the context of nucleic acid hybridization, it will be apparent to one skilled in the art of biochemical instrumentation and analysis that this embodiment could be equally applied to other process in which a polar analyte is contacted with a binding complement, e.g., antibody-antigen pairs, receptor-ligand pairs, biotin-avidin pairs, and the like.

In yet another preferred embodiment of the methods of the present invention, during or subsequent to the concentration of the polar analyte in a concentration zone, the polar analyte is detected using a detector, for example a fluorescence detector. In this embodiment, the pre-detection concentration step can lead to enhanced detectability of the polar analyte thereby leading to a more sensitive measurement, or the opportunity to use a less sophisticated or expensive detection system, e.g., UV absorbence rather than laser-induced fluorescence. Where detection takes place during the concentration process, the concentration process may be monitored in real time.

In yet another preferred embodiment of the invention, during or subsequent to the concentration of the polar analyte, the concentrated polar analyte is contacted with a reactant and a chemical reaction is effected between the reactant and the concentrated polar analyte. Such reactions may include chemical, immunological, or enzymatic processes, e.g., analyte labeling, protein digestion, DNA digestion or fragmentation, DNA synthesis, and the like. The concentration step may lead to an increased reaction rate or enhanced detectability of the reaction products.

III. DEVICES

As is evident based on the foregoing discussion of the various preferred methods according to the present invention, a wide variety of devices may be constructed to carry out the methods. The particular elements, lay-out, dimensions, materials, and experimental conditions used to construct and operate the devices of the invention may vary depending on the particular method or application being addressed.

Generally, a device according to the present invention includes a means for generating an alternating electric field and a means for effecting the relative translation of a polar analyte with respect to the alternating electric field along a translation path. The device is constructed so that in operation a concentration zone is formed at the intersection of the translation path and the alternating electric field. Several exemplary devices according to the present invention are described below.

Figure 2A:
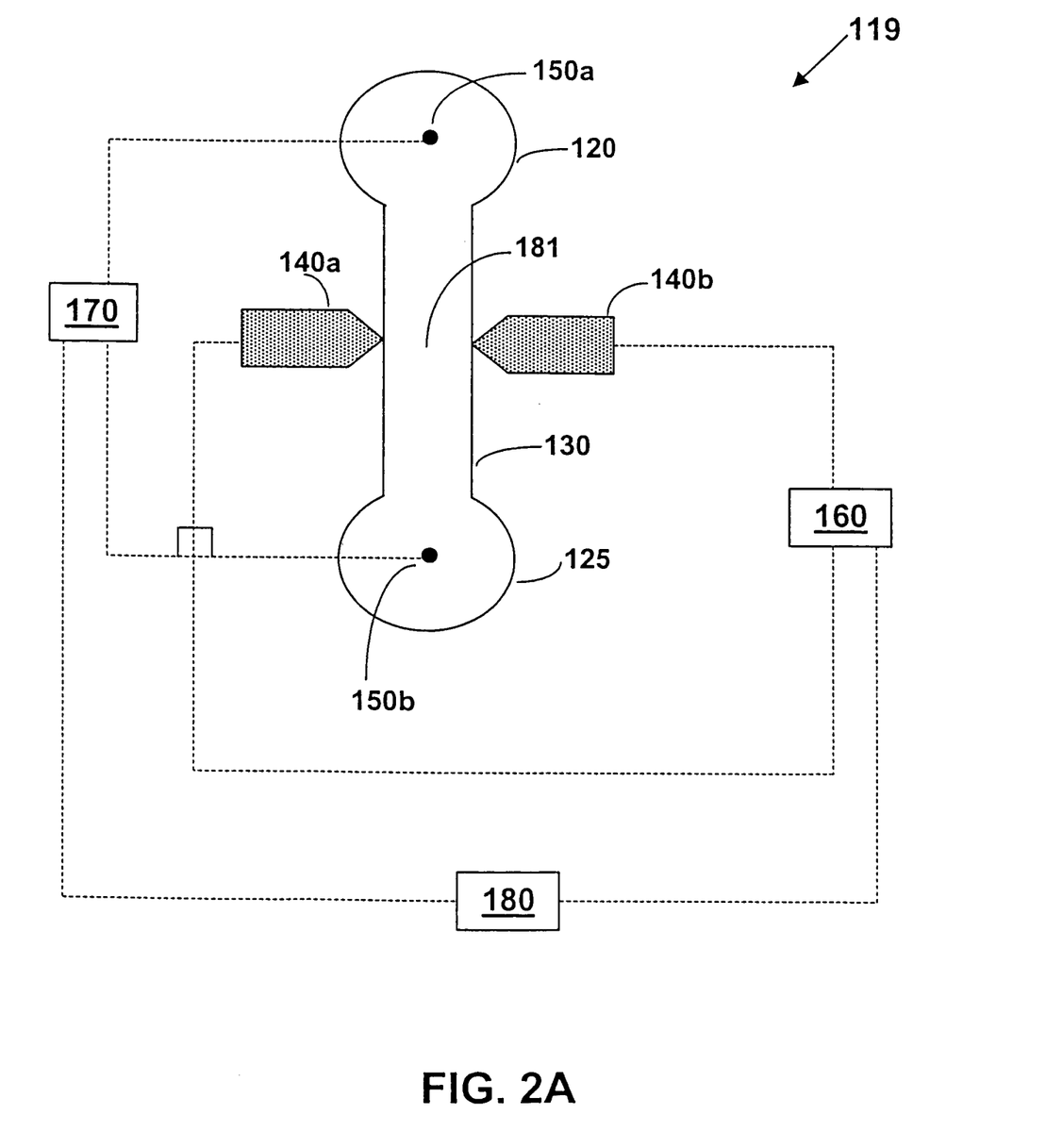
FIG. 2A is a schematic representation of a preferred microfluidic concentration and detection device according to the present invention.

FIG. 2A shows a schematic representation of an exemplary microfluidic concentration and detection device 119 according to the present invention. The device 119 comprises an analyte loading reservoir 120, a translation channel 130, and a waste reservoir 125, such that the analyte loading reservoir 120 is in fluid communication with the waste reservoir 125 through the translation channel 130. Both the analyte loading reservoir 120 and the waste reservoir 125 contain electrodes 150a and 150b for effecting the electrokinetic translation of an analyte along the translation channel 130. The electrodes 150a and 150b are each connected to a power supply 170 for providing a voltage difference between electrodes 150a and 150b and thereby effecting an electric field along the translation channel 130 sufficient to cause the electrokinetic translation of an analyte along the translation channel 130. The device 119 further comprises a second pair of electrodes 140a and 140b located at opposite sides of the translation channel 130 so as to effect an alternating electric field across the width of the translation channel 130. The electrodes 140a and 140b are connected to an alternating field power supply 160 for providing a time-variant voltage difference between electrodes 140a and 140b and thereby effecting an alternating electric field substantially across the translation channel 130. A concentration zone 181 is located between electrodes 140a and 140b. Optionally, the device 119 further includes a detector (not shown) positioned such that material located in the concentration zone 181 may be detected. In addition, the device 119 further optionally includes a computer 180 connected to the power supply 170, the alternating field power supply 160, and to the detector (not shown) to control and monitor the operation of the device and to manage the acquisition, analysis, and presentation of data.

Figure 2B:
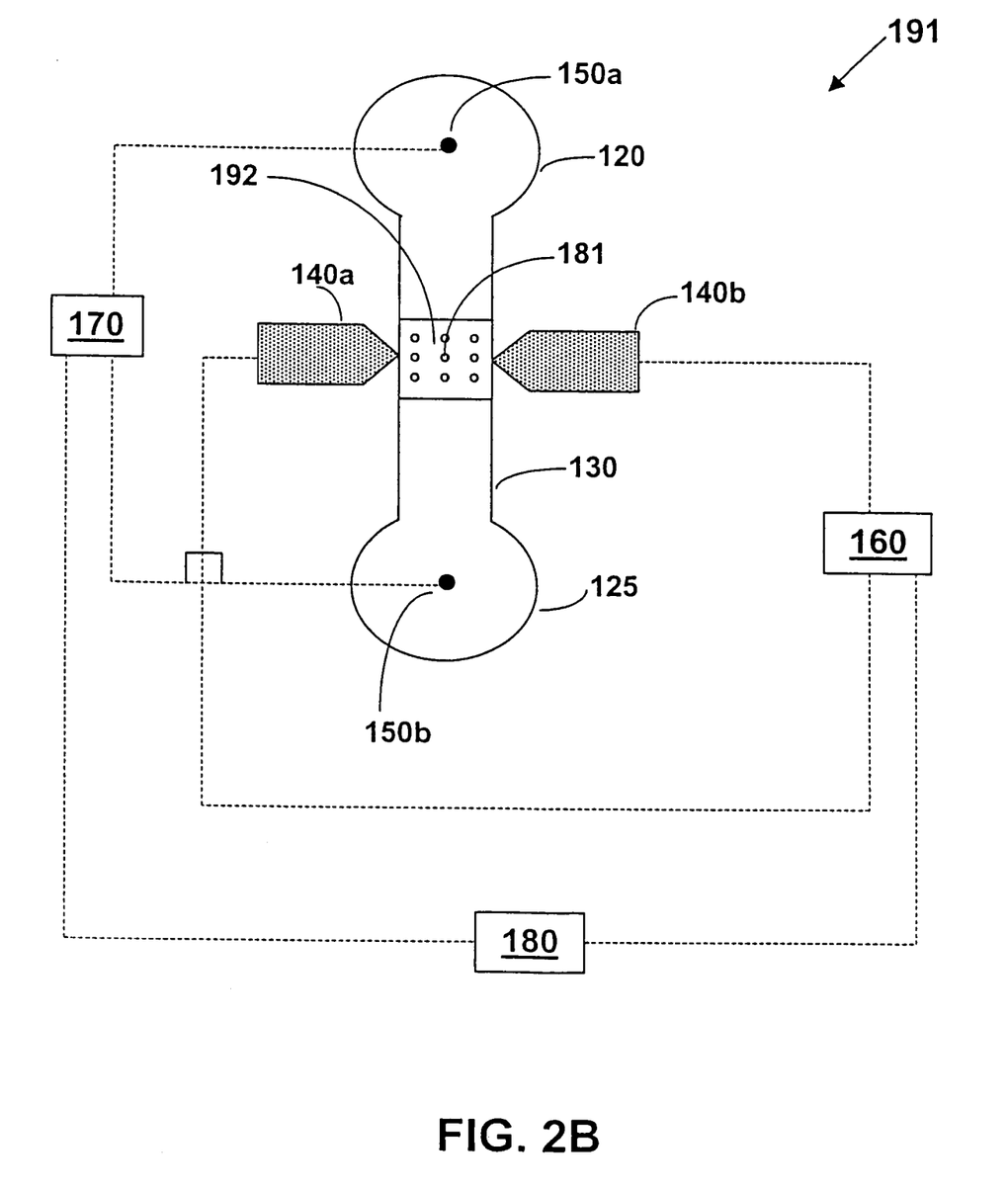
FIG. 2B is a schematic representation of a preferred microfluidic concentration, hybridization, and detection device according to the present invention.

FIG. 2B shows a variant of the device described in FIG. 2A 191 in which a polynucleotide hybridization array 192, or an array of any other support-bound binding moiety, is located in the concentration zone 181 located between electrodes 140a and 140b. The location of the hybridization array 192 is such that an analyte to be contacted with the array is concentrated in the concentration zone 181 adjacent to the array prior to hybridization in order to increase the rate of mass transfer of the analyte to the array and enhance the detectability of the hybridized analyte.

In operation, the device 191 works generally as follows. The translation channel 130 and the waste reservoir 125 are filled with a supporting medium, e.g., a low ionic strength buffered electrolyte solution, and a polar analyte is placed in the analyte loading reservoir 120, e.g., using a conventional micropipette. Then, power supply 170 is activated thereby causing the electrokinetic translation of the analyte out of the analyte loading reservoir 120 and into the translation channel 130. Next, before the analyte reaches the concentration zone 181 located generally between pair of electrodes 140a and 140b, the alternating field power supply 160 is activated. As the analyte moves through the translation channel 130 into the concentration zone 181 formed by the intersection of the alternating electric field and the translation channel 130, the polar analyte is trapped and concentrated in the concentration zone. This process is continued until the desired amount of analyte is located in the concentration zone. Finally, the amount of polar analyte in the concentration zone is detected by the detector. Alternatively, the detector monitors the concentration zone throughout the process in order to detect the time course of the concentration process. Or, in the device 191 shown in FIG. 2B, the concentration process is continued until the concentration of the polar analyte is sufficient to effect the hybridization step.

Figure 2C:
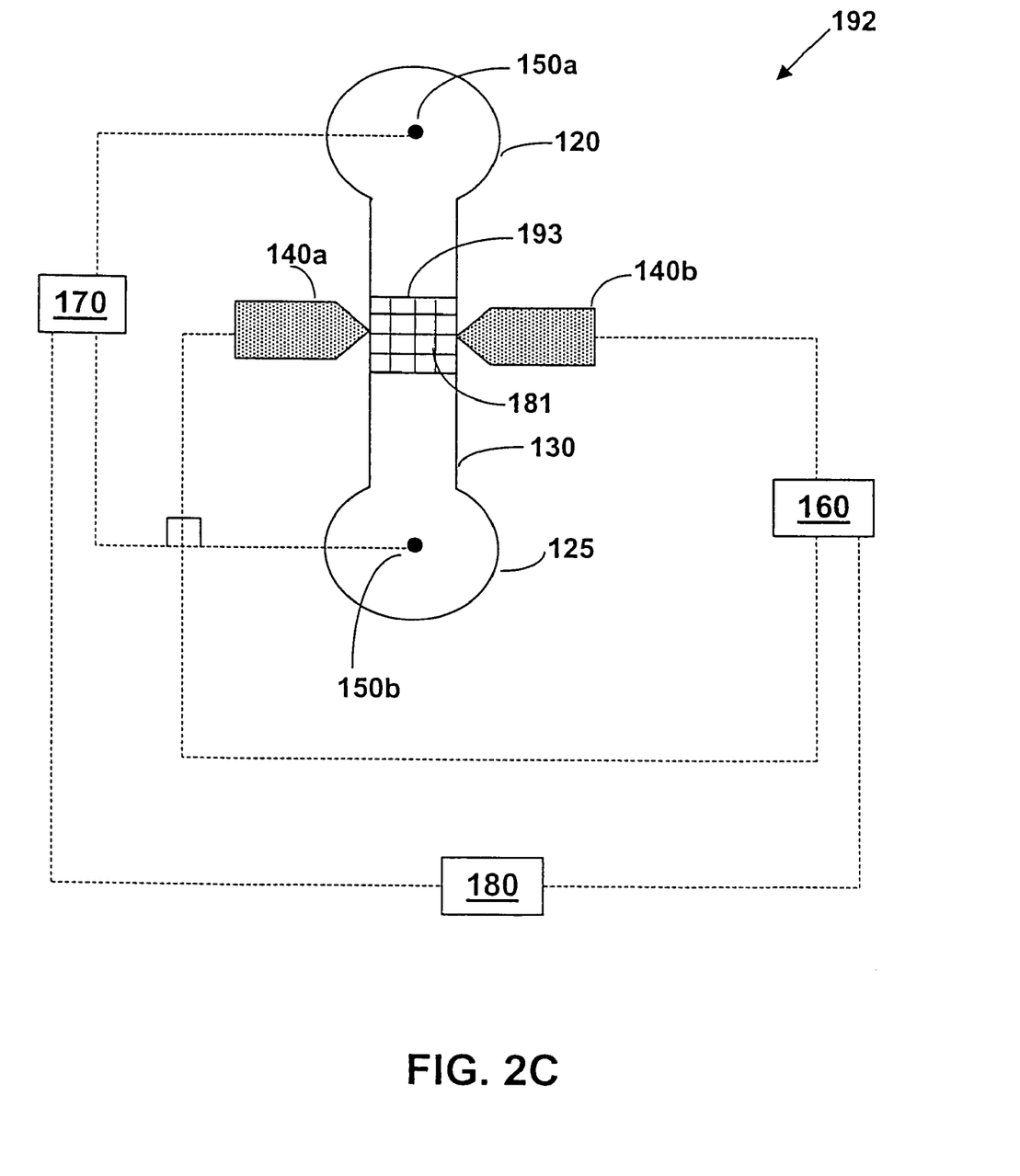
FIG. 2C is a schematic representation of a preferred microfluidic concentration device including a frit located in the concentration zone.

FIG. 2C shows another variant of the device described in FIG. 2A 192 in which a frit 193 is located in the concentration zone 181 located between electrodes 140a and 140b. While the theoretical explanation for this highly unexpected and beneficial phenomena is not well understood, and the present invention is not intended to be limited in any way by the following or any other theoretical explanation, it is thought by the inventors that the frit 193 creates spatial nonuniformities in the alternating electric field which, in certain circumstances, serves to enhance the concentration effect of the invention. The frit 193 has a porous structure comprising through-pores containing a fluid medium such that material can be transported through the frit. Preferably, the pore structure of the frit comprises pores having effective internal diameters of between 0.5 and 50 μm.

In one embodiment, the frit is made up of an insulating matrix such that the AC electrical conductivity of the insulating matrix is substantially less than the AC electrical conductivity of the fluid medium contained in the pores of the frit. Preferably, the electrical conductivity of the fluid medium is 3 times greater than that of the insulating matrix, and more preferably between 10 and 1000 times greater than that of the insulating matrix. The insulating matrix may be formed from any insulating material that can be fabricated into a frit. Exemplary materials include plastics, ceramics, and the like. Preferably, the insulating matrix is a plastic such as polymethylmethacrylate.

In an alternative embodiment, the frit includes electrically-conductive particles suspended in the insulating matrix such that there exists a plurality of electrically isolated regions each containing one or more conductive particles. In an ideal case, each particle would be electrically isolated from all other particles by the insulating matrix. The conductive particles may be formed from any conductive or semi-conductive material, but preferably the particles are metallic, e.g., silver, gold, platinum, copper, and the like, or semiconductor materials, e.g., gallium arcinide. In a preferred embodiment, the particles are substantially spherical and have a diameter of between about 0.5 μm to about 50 μm.

Methods for fabricating frits according to the present invention are well known. Briefly, one exemplary preferred frit fabrication procedure is as follows. Dissolve 1 gram of Plexiglass in 250 ml of chloroform at room temperature to form a Plexiglass/chloroform mixture. Next, mix 20 grams of 150 mesh (99.5%) copper basis copper particles (Alfa AESAR, stock # 10160) with 2 ml of the plexiglass/chloroform mixture to form a particle suspension. The metal particles should be approximately 2-10 µm in diameter. Mixing should be performed at room temperature by swirling the suspension until it becomes evenly mixed for approximately 5 minutes. To form the frit, aspirate a 2-5 mm length of the mixture into a micropipet (Micropipetts calibrated color coded disposable, VWR Scientific, cat # 53432-921, Size 100 ul) using a conventional pipette bulb. Allow the aspirated suspension to dry partially for approximately 5 minutes and then push the suspension farther into the micropipette using a rigid wire or rod. Finally, allow the frit to dry for an additional 30 minutes at room temperature. The frit may then be used in situ or be mechanically removed from the micropipette.

Figure 3A:
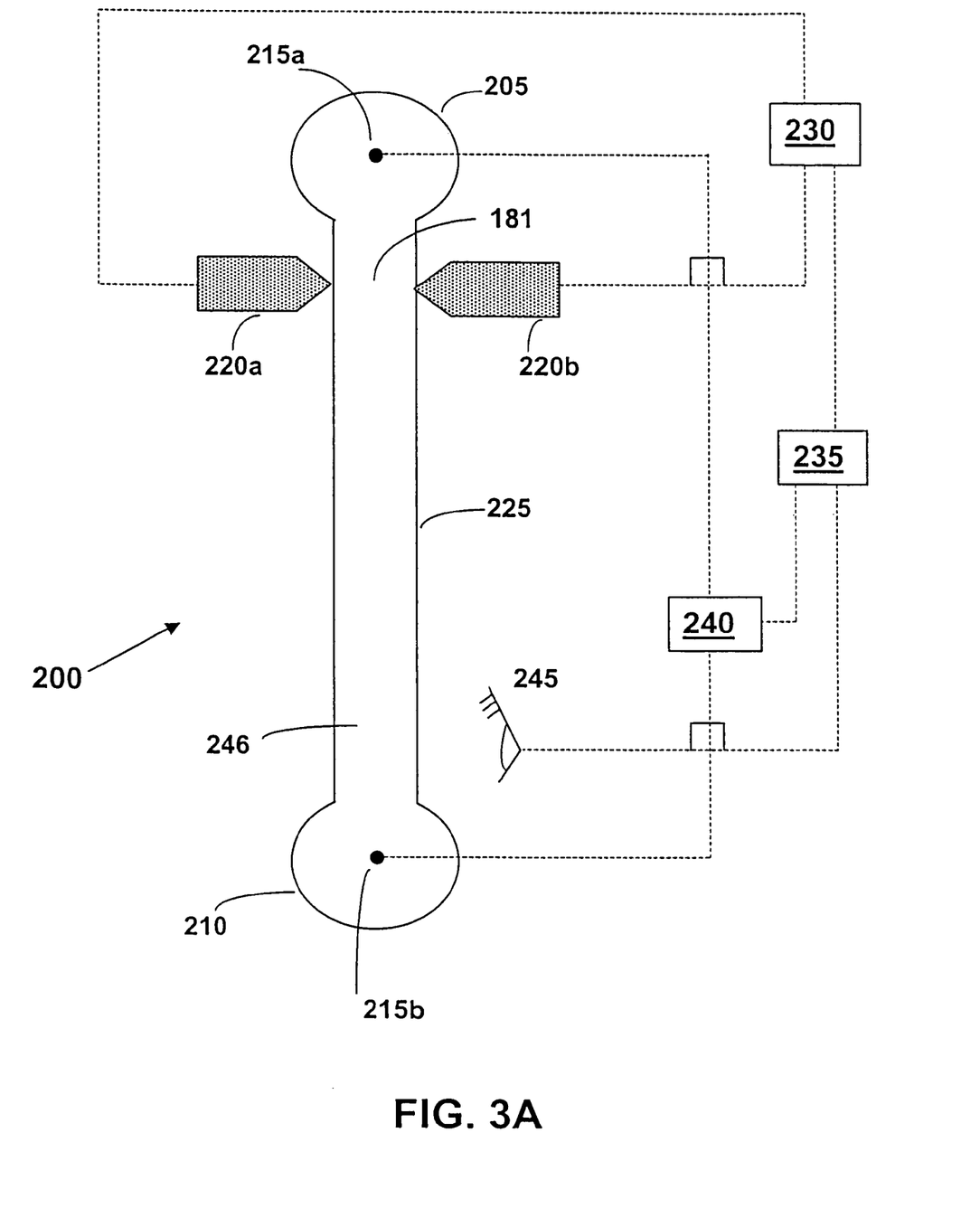
FIG. 3A is a schematic representation of a preferred microfluidic concentration and electrokinetic separation device according to the present invention.

FIG. 3A shows a schematic representation of another exemplary microfluidic device 200 according to the present invention. The device 200 comprises an analyte loading reservoir 205, an electrokinetic separation channel 225, and a waste reservoir 210, such that the analyte loading reservoir 205 is in fluid communication with the waste reservoir 210 through the electrokinetic separation channel 225. The analyte loading reservoir 205 and the waste reservoir 210 contain electrodes 215$a$ and 215$b$, respectively, for effecting an electrokinetic translation of a polar analyte along the electrokinetic separation channel 225. Electrodes 215$a$ and to 215$b$ are connected to power supply 240. The device further comprises trapping electrodes 220$a$ and to 220$b$ for effecting an alternating electric field between electrodes 220$a$ and 220$b$. Electrodes 220$a$ and to 220$b$ are connected to alternating-voltage power supply 230. The device further comprises a detector 245 located at a distal end of the electrokinetic separation channel 225 relative to the loading reservoir 205 for detecting the polar analyte in a detection zone 246 after the electrokinetic separation is substantially complete. Optionally, the device 200 includes a computer 235 which is connected to power supply 230, power supply 240, and detector 245, to control and monitor the operation of the device and to manage acquisition, analysis, and presentation of data. The device 200 may optionally further include a second alternating voltage power supply and pair of electrodes (not shown) located proximate to the detection zone 246 for trapping and concentrating the separated components of the polar analyte prior to or during detection in order to further increase the detectability of the separated components.

In operation, the device 200 works as follows. First, the electrokinetic separation channel 225 and the waste reservoir 210 are filled with an electrolyte solution capable of supporting the electrokinetic translation of the polar analyte along the electrokinetic separation channel 225. Then, the analyte loading reservoir 205 is filled with an analyte, for example using a conventional micropipette. Next, power supply 240 is activated in a forward polarity to initiate the electrokinetic translation of the polar analyte along the electrokinetic separation channel 225. In addition, power supply 230 is activated in order to establish the alternating electric field used to trap and concentrate the polar analyte in the concentration zone 181 located approximately between electrodes 220$a$ and to 220$b$. Optionally, to increase the amount of analyte trapped in the concentration zone, the polarity of power supply 240 may be cycled between the forward polarity and a reverse polarity such that the polar analyte is translated back and forth through the concentration zone. Once a sufficient amount of the polar analyte is located and concentrated in the concentration zone, the power supply 240 is activated in the reverse polarity thereby drawing uncaptured material out of the electrokinetic separation channel 225 and back in to loading reservoir 205. At this point, any analyte remaining in analyte loading reservoir 205 may be removed and replaced with an appropriate electrolyte solution. Next, power supply 230 is turned off and the electrokinetic separation process is continued along the electrokinetic separation channel 225 until the components of the polar analyte are transported to the detection zone 246 and detected by the detector 245.

Figure 3B:
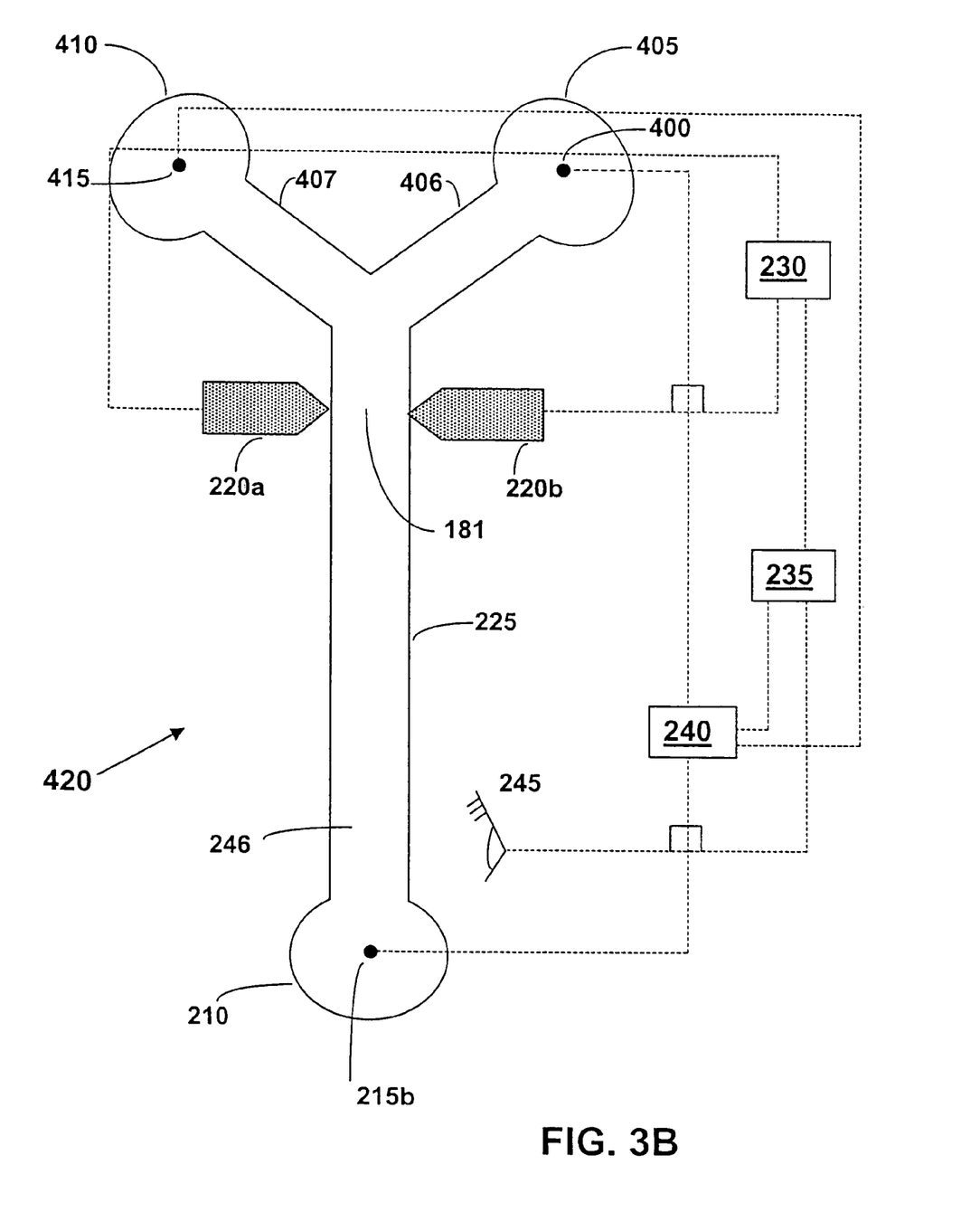
FIG. 3B is a schematic representation of an alternative preferred microfluidic concentration and electrokinetic separation device according to the present invention.

FIG. 3B shows a schematic representation of yet another exemplary microfluidic device 420 according to the present invention. The device 420 is a variant of the device 200 of FIG. 3A in which the single analyte loading reservoir 205 in device 200 is replaced with a pair of reservoirs: an analyte loading reservoir 405 and an analyte waste reservoir 410. The analyte loading reservoir 405 contains electrode 400 and the analyte waste reservoir 410 contains electrode 415. Analyte loading reservoir 405 is connected to the electrokinetic separation channel 225 by branch channel 406, and analyte waste reservoir 410 is connected to electrokinetic separation channel 225 by branch channel 407. Other elements of the device 420 are as described with respect to device 200 in FIG. 3A.

In operation, the device 420 works as follows. First, the electrokinetic separation channel 225, the waste reservoir 210, the branch channels 407 and 406, and the analyte waste reservoir 410 are filled with an electrolyte solution capable of supporting the electrokinetic translation of the polar analyte along the electrokinetic separation channel 225. Then, the analyte loading reservoir 205 is filled with an analyte, for example using a conventional micropipette. Next, power supply 240 is activated in a forward polarity to effect a potential difference between electrodes 400 and 215$b$, to initiate the electrokinetic translation of the polar analyte through branch channel 406 and along the electrokinetic separation channel 225 and into concentration zone 181. As before, power supply 230 is activated in order to establish the alternating electric field used to trap and concentrate the polar analyte in the concentration zone 181 located substantially between electrodes 220$a$ and to 220$b$. Optionally, the polarity of power supply 240 may be cycled between the forward polarity and a reverse polarity such that the polar analyte is translated back and forth through the concentration zone. Once a sufficient amount of the polar analyte is located and concentrated in the concentration zone, the power supply 240 is activated in the reverse polarity to effect a potential difference between electrodes 415, 400 and 215$b$ such that uncaptured material is drawn out of the electrokinetic separation channel 225 and the analyte loading reservoir 405 and into the analyte waste reservoir 410. Optionally, after sweeping the uncaptured analyte into analyte waste reservoir 410, analyte present in waste reservoir 415 may be removed and replaced with an appropriate electrolyte solution. Next, power supply 230 is turned off and the electrokinetic separation process is continued along the electrokinetic separation channel 225 between electrodes 400 and 215$b$ until the components of the polar analyte are transported to the detection zone 246 and detected by the detector 245.

The fluidic channels used in many of the preferred devices of the invention may be any channel capable of supporting a sample containing a polar analyte and solvent or other supporting media required to carry out a method of the invention. The channels may be discrete, for example individual capillary tubes, or formed as part of an integrated microfluidic device, e.g., channels etched in a glass substrate. Preferably, the fluidic channels are formed as part of an integrated microfluidic device including one or more intersecting channels and reservoirs. Exemplary microfluidic devices, and several alternative methods for device fabrication, are disclosed in Soane and Soane, U.S. Pat. Nos. 5,750,015 and 5,126,022; Manz, U.S. Pat. Nos. 5,296,114 and 5,180,480; Junkichi et al., U.S. Pat. No. 5,132,012; and Pace, U.S. Pat. No. 4,908, 112. Other references describing microfluidic devices include Harrison et al., *Science,* 261: 895 (1992); Jacobsen et al., *Anal. Chem.* 66: 2949 (1994); Effenhauser et al., *Anal. Chem.* 66:2949 (1994); and Woolley and Mathies, *P.N.A.S. USA,* 91:11348 (1994). A general discussion of microfabrication techniques is provided by Madou in *Fundamentals of Microfabrication*, CRC Press, Boca Raton, Fla. (1997).

The fluidic channels may be present in the device in a variety of configurations, depending on the particular application being addressed. The internal volume of a channel will preferably range from about 1 nl to about 10 µl, and more preferably from about 10 nl to about 2 µl. The length of a channel will generally range from about 1 mm to about 50 cm, usually between about 5 cm to 30 cm. However, in certain applications, channels may have a length up to or greater than 100 cm, e.g., where the channel is used as an electrokinetic or chromatographic separation channel. The cross-sectional dimensions (e.g., width, height, diameter) will range from about 1 µm to about 400 µm, usually from about 20 µm to about 200 µm. The cross-sectional shape of the channel may be any cross-sectional shape, including but not limited to circular, ellipsoid, rectangular, trapezoidal, square, or combinations of the foregoing shapes. The fluidic channels may be straight, serpentine, helical, spiral, or any other configuration, depending on the requirements of a particular application. For example, if it is desired to construct a long fluidic channel in a small substrate, it may be advantageous to construct a channel having a spiral or serpentine shape.

The fluidic channels of the device may optionally comprise, and usually will comprise, fluid reservoirs at one or both termini, i.e., either end, of the channels. Where reservoirs are provided, they may serve a variety of purposes including a means for introducing various fluids into the channel, e.g., buffer, elution solvent, sieving media, reagent, rinse or wash solutions; means for receiving waste fluid from a channel, e.g., an electrokinetic flowpath; or, as electrode reservoirs for contacting an electrode with an electrolyte and for supplying ions to support an electrokinetic process. Generally, the reservoirs will have a volume of between 1 µl and 100 µl, preferably between about 1 µl and 10 µl. Larger reservoirs may be desirable if the reservoirs serve multiple fluidic channels.

The subject devices may also optionally comprise an interface system for assisting in the introduction of an analyte into the device. For example, where the analyte is to be introduced into the device using a syringe, the interface system may comprise a syringe interface which serves as a guide for the syringe needle into the device, e.g., as a seal over an analyte introduction reservoir.

Depending on the particular application, configuration, and materials from which the device is fabricated, a detection region for detecting the presence of a particular analyte may be included in the device, e.g., element 246 in FIG. 3. For example, preferably at least one region of the electrokinetic channel includes a detection region that is fabricated from a material that is optically transparent, generally allowing light of wavelengths ranging from 180 to 1500 nm, usually 250 to 800 nm, to be transmitted through the material with low transmission losses, i.e., less than about 20%, preferably less than about 5%. Suitable optically transparent materials include fused silica, certain optically-clear plastics, quartz glass, borosilicate glass, and the like.

The subject devices according to the present invention may be fabricated from a wide variety of materials, including glass, fused silica, acrylics, thermoplastics, silicon, and the like. Preferably, the materials will have high dielectric breakdown potential, e.g., greater than about 100 kV/cm, be mechanically rigid, be chemically compatible with the polar analyte and any associated solvents or media, and have a low dielectric loss factor, e.g., less than about 0.05 at 1 MHz. The various components of the integrated device may be fabricated from the same or different materials, depending on the particular use of the device, the economic concerns, solvent compatibility, optical clarity color, mechanical strength, mechanical features, electrical properties, thermal properties, and the like. For example, a planar substrate comprising microfluidic flowpaths and a cover plate may be fabricated from the same material, e.g., polymethylmethacrylate (PMMA), or different materials, e.g., a substrate of PMMA and a cover plate of glass. For applications where it is desired to have a disposable integrated device, due to ease of manufacture and cost of materials, the device will typically be fabricated from a plastic. For ease of detection and fabrication, the entire device may be fabricated from a plastic material that is optically transparent with respect to the optical wavelengths used for detection. Also of interest in certain applications are plastics having low surface charge under conditions of electrophoresis. Particular plastics useful for the fabrication of disposable devices according to the present invention include but are not limited to polymethylmethacrylate, polycarbonate, polyethylene terepthalate, polystyrene or styrene copolymers.

Optionally, the surface properties of materials used to fabricate the devices may be altered in order to control analyte-wall interactions, electroendoosmosis, bonding properties, or any other surface-mediated property of the materials. The surface modifications may be based on covalent attachment of coating agents, or physical attachment, e.g., by ionic, hydrophobic, or van der Waals interactions. Exemplary surface modification techniques are described elsewhere, e.g., Hjerten, U.S. Pat. No. 4,680,201; Cobb et al., *Anal. Chem.,* 62: 2478-2483 (1990); van Alstine et al., U.S. Pat. No. 4,690, 749; and Belder and Schomburg, *Journal of High Resolution Chromatography,* 15: 686-693 (1992).

The devices according to the present invention may be fabricated using any convenient means used for fabricating like devices. In a preferred embodiment of the invention, conventional molding and casting techniques are used to fabricate the devices. For example, for devices prepared from a plastic material, a silicon mold master which is a negative for the channel structure in the planar substrate of the device can be prepared by etching or laser micromachining. In addition to having a raised ridge which will form the channel in the substrate, the silica mold may have a raised area which will provide for a cavity into the planar substrate for forming reservoirs or other fluidic features. Where convenient, the procedures described in U.S. Pat. No. 5,110,514 may be employed. A cover plate may be sealed to the substrate using any convenient means, including ultrasonic welding, adhesives, etc.

Alternatively, the devices may be fabricated using photolithographic techniques as employed in the production of microelectronic computer chips as follows. First, a substrate support such as a polymethylmethacrylate card approximately the size of a conventional credit card is provided. The surface of the card itself is not electrically conducting nor is the card. On the card is first deposited a thin layer of an electrically conducting material, e.g., a metal. The coating may be applied by a variety of different techniques known to those skilled in the art and may be comprised of a variety of different types of materials provided they are capable of conducting electricity and preferably chemically inert, e.g., platinum, gold, and the like. The layer is preferably thin; on the order of 100 angstroms to a few microns of thickness. The electrically conducting layer is then coated with a layer of material which is both light-sensitive and non-conducting. Once the light-sensitive, non-conducting layer completely covers the electrically conducting layer, a mask is applied to the surface of the light-sensitive, non-conducting layer. After the mask covers the layer, it is exposed to light resulting in a pattern of portions of the light-sensitive material being solvent soluble and portions being solvent insoluble. The soluble portions are washed away and the exposed electrically conducting material etched away leaving traces of wires and connectors to the wires under the insoluble portion of the light sensitive material. The underlying electrically conducting material will provide electrode connections to the fluidic channels and reservoirs. By removing a portion of the insoluble material from the ends or connectors of the electrically conducting traces remaining from the electrically conducting layer, electrical connection can be made with the electrode connectors to the fluidic elements. In addition the electrode traces are protected from wear and abrasion by the protective coating. As will be apparent to those skilled in the art, the mask utilized in the above production procedure can be produced so as to provide essentially an unlimited number of different electrode connections to the device, e.g., see S. M. Sze, *VLSI Technology, Second Edition*, McGraw-Hill, New York, N.Y. (1988).

Where the devices are formed from glass, standard etching process may be used, e.g., K. Fluri et al., *Anal. Chem.*, 66: 4285-4290 (1996); Z. Fan and D. J. Harrison, *Anal. Chem.*, 66: 177-184 (1994).

Alternatively, rather than utilizing the photolithographic or molding and casting techniques generally described above to fabricate the devices of the present invention, it is possible to utilize other fabrication techniques such as employing various types of laser technologies and/or other technologies such as silk-screening and vapor deposition which make it possible to provide extremely small (in size) and large numbers of electrodes and fluidic channels, or lamination, or extrusion techniques.

Generally, the fluidic channels will contain a supporting medium to support the analyte. The medium may be an organic solvent, a buffer solution, a polymeric solution, a surfactant micellular dispersion, or gel of the type generally used in connection with biochemical separation techniques. Preferably, the medium will have a low ionic strength, e.g., below about 100 mM salt, more preferably below about 10 mM salt, and comprise a solvent having a low dielectric constant, e.g., below about 80. A particularly preferred medium comprises an entangled aqueous polymer solution, e.g., Madabhushi et al, U.S. Pat. No. 5,567,292.

The electrodes used in the devices of the invention, e.g., to effect the alternating electric field, may be fabricated using conventional methods from conventional materials. Exemplary methods for electrode fabrication include photolithography, silkscreen techniques, and a simple wire electrode. Preferably, the materials used to form the electrodes are electrically conductive and chemically inert. Particularly preferred materials include gold, platinum, tungsten, and the like.

Figure 4:
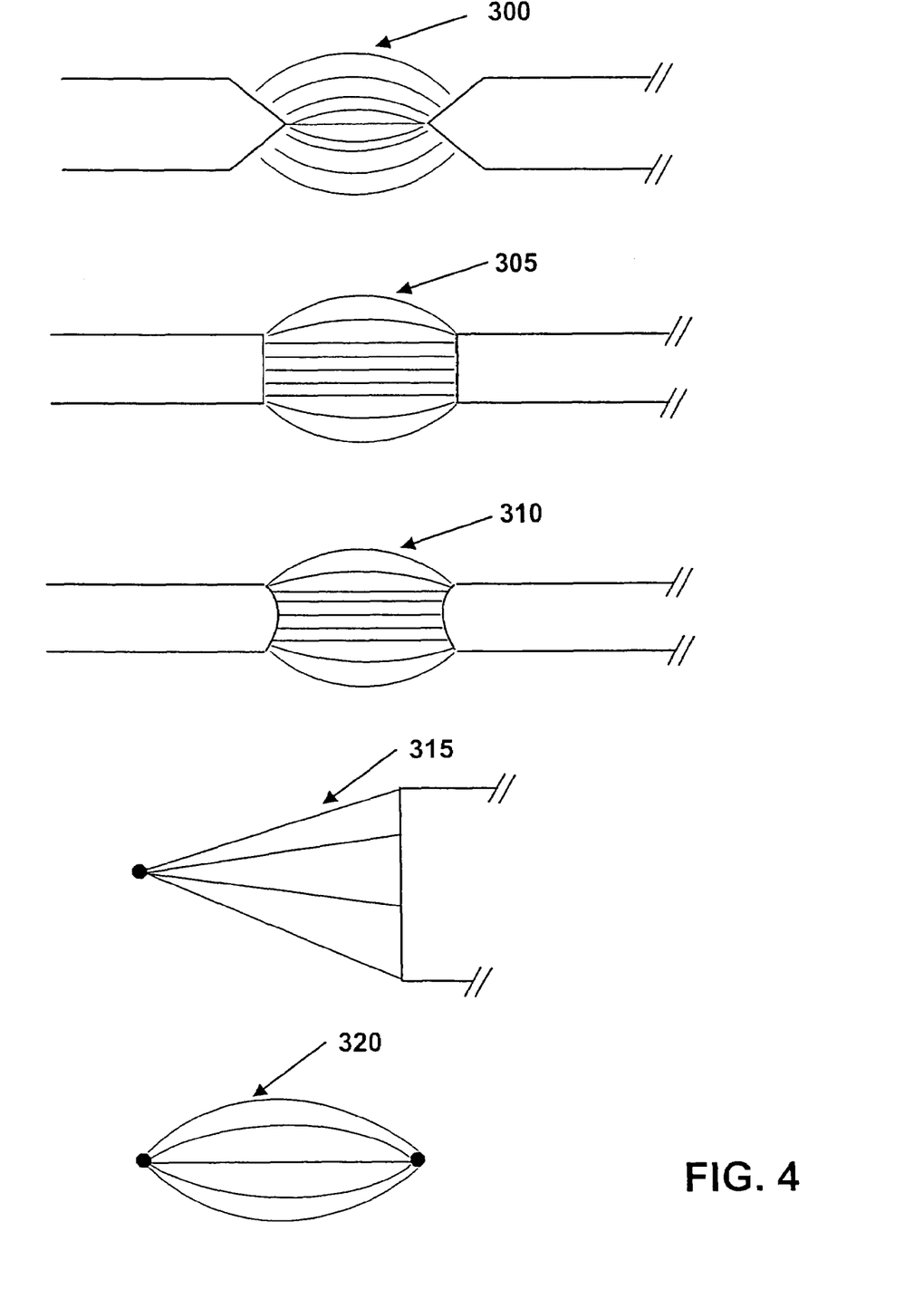
FIG. 4 is a schematic representation of several exemplary electrode configurations adapted for use in the present invention.

Preferably the electrodes used to effect the alternating electric field have a shape which serves to form an electric field that results in a single, well-defined concentration zone having the desired dimensions. FIG. 4 shows several exemplary electrode geometries; 300, 305, 310, 315, and 320. The spacing of the electrodes is chosen so as to generate an electric field having sufficient strength to trap a polar analyte of interest but not so high as to cause excessive bubble formation at the electrodes, e.g., see Washizu et al., *IEEE Transactions on Industry Applications,* 30 (4): 835-843 (1994). Generally, the spacing between the electrodes is preferably between about 50 μm and 2 mm.

Preferably, the electrodes used to effect the alternating electric field do not protrude into the translation path or otherwise come into direct physical contact with the translation path. Rather, the electrodes are preferably positioned such that the alternating electric field produced between the electrodes intersects the translation path, but the electrodes themselves are physically removed from the translation path, e.g., using an isolation layer or an electrical connection through a conductive bridge. Exemplary materials useful for forming an isolation layer include $SiO_2$, $Al_2O_3$, polyimide, diamond, glass, and the like. Isolating the electrodes from the translation path is preferred because it serves to minimize the extent to which the electrodes may become fouled by the analytes or any other material present in the translation path, or become passivated due to oxidation or other chemical transformation of the electrode surface.

The means for effecting an alternating electric field may include any conventional alternating current power supply using conventional electrical connectors. An exemplary alternating current power supply suitable for use in the present invention is a Model 33120A 15 MHz Function/Arbitrary Waveform Generator function generator from Agilent Technologies. The means for effecting an alternating electric field further includes the above-described electrodes and electrical connections between the electrodes and the alternating current power supply.

The electrodes may be fabricated and integrated into the devices of the invention using any one of a number of conventional techniques. For example, wire electrodes may be mechanically attached to the device, electrodes may be incorporated into the device during a lamination step or during a casting step, electrodes may be deposited onto the device using plasma deposition or electrochemical deposition techniques.

As discussed above, certain embodiments of the present invention include a detection system for detecting an analyte during or subsequent to an analysis. Any sort of conventional detection system may be used with the present invention, including systems for measuring fluorescence, radioactivity, optical absorbence, fluorescence polarization, electrical conductivity, electrochemical properties, refractive index, and the like. A particularly preferred detection system employs laser-excited fluorescence.

In a preferred embodiment of the present invention, the channels, reservoirs, or concentration zone of the microfluidic device are maintained at a controlled temperature using a temperature control system. For example, temperature control may be desirable in order to increase the reproducibility of an analysis, control the properties of a medium or analyte, or to speed up an analysis. A preferred temperature control system may include a heating element, e.g., a resistive heating element in combination with a fan, a cooling device, e.g., a Peltier device or other conventional refrigeration device, an enclosed thermally-isolated chamber, one or more temperature measurement sensors, and a programmable feedback control system. Preferably, the temperature control system is connected to a computer for controlling and monitoring the overall system.

The devices of the present invention may be used in combination with robotic systems to automate certain steps of a process, e.g., a robot may be used to manipulate a plurality of microfluidic devices for high-throughput multi-device applications, or to introduce an analyte into a device of the invention, or to transfer a medium into or out of the device. Such robots may be any kind of conventional laboratory robot, preferably with fluid-handling capability, e.g., a Beckman BioMek system.

In certain embodiments of the present invention, a computer is used to monitor or control various aspects of the device including: controlling the operation of the components of the device, e.g., power supplies, temperature controller, pumps, etc.; controlling systems associated with the device, e.g., laboratory robots; monitoring the performance of the device, e.g., measuring electric field strengths, temperatures, or pressures; managing of data acquisition, data analysis, and data presentation activities; or providing a convenient user interface for the programmable operation of the device. The computer of the present invention may be any type of conventional programmable electronic computer, e.g., a personal computer. The computer may be connected to other elements of a system through conventional devices, e.g., an A/D converter.

All publications, patents, and patent applications mentioned herein are hereby incorporated by reference to the same extent as if each individual publication, patent, or patent application was specifically and individually indicated to be incorporated by reference.

Although only a few embodiments have been described in detail above, those having ordinary skill in the art of chemical instrumentation will clearly understand that many modifications are possible in the preferred embodiments without departing from the teachings thereof. All such modifications are intended to be encompassed within the scope of the following claims.

We claim:

1. A device for manipulating a plurality of cells, comprising:
    (a) a translation channel, said translation channel having (i) first and second end regions, and (ii) first and second lateral side regions;
    (b) a first set of electrodes, wherein at least one electrode of said first set is disposed toward the first end region, and at least one other electrode of said first set is disposed toward the second end region;
    (c) a second set of electrodes, wherein at least one electrode of said second set is disposed toward the first lateral side region, and at least one other electrode of said second set is disposed toward the second lateral side region;
    (d) a first power supply disposed for electrical communication with said first set of electrodes and a second power supply disposed for electrical communication with said second set of electrodes;
    (e) a computer disposed for communication with said device, said computer being operable to establish a translational electrical field lengthwise along at least a portion of said translation channel and a trapping electrical field transverse to said translational electrical field, with said translational and trapping electrical fields crossing one another at an intersection defining a concentration zone; and
    (f) a detector positioned to detect cells in the concentration zone, wherein the computer is disposed for operable communication with the detector, and wherein the computer is configured to alter at least one of the translational electric field and the trapping electric field in response to data received from the detector.

2. The device of claim 1, wherein the computer alters the translational electric field to effect translation of the cells along the translation channel such that at least a portion of the cells pass through the concentration zone.

3. The device of claim 1, further comprising a temperature control system.

4. The device of claim 3, wherein the temperature control system is in thermal communication with the concentration zone.

5. A device for manipulating a plurality of cells, comprising:
    (a) an elongated channel including (i) first and second end regions, and (ii) first and second lateral side regions;
    (b) a first set of electrodes, wherein at least one electrode of said first set is disposed toward the first end region, and at least one other electrode of said first set is disposed toward the second end region;
    (c) a second set of electrodes, wherein at least one electrode of said second set is disposed toward the first lateral side region, and at least one other electrode of said second set is disposed toward the second lateral side region;
    (d) a first power supply disposed for electrical communication with said first set of electrodes and a second power supply disposed for electrical communication with said second set of electrodes;
    (e) a computer disposed for communication with said device, said computer being operable to establish a translational electrical field lengthwise along at least a portion of said elongated channel and a trapping electrical field transverse to said translational electrical field, with said translational and trapping electrical fields crossing one another at an intersection defining a concentration zone; and
    (f) a detector positioned to detect cells in the concentration zone, wherein the computer is disposed for operable communication with the detector, and wherein the computer is configured to alter at least one of the translational electrical field and the trapping electrical field in response to data received from the detector.

6. The device of claim 5, further comprising a temperature control system.

7. The device of claim 6, wherein the temperature control system is in thermal communication with the concentration zone.

8. A method of manipulating a plurality of cells, comprising:
    (a) establishing a translational electrical field lengthwise along at least a portion of a translation path and a trapping electrical field transverse to said translational electrical field, with said translational and trapping electrical fields crossing one another at an intersection defining a concentration zone;
    (b) detecting the presence or absence of one or more cells in the concentration zone; and
    (c) altering at least one of the translational electrical field and the trapping electrical field in response to data received during the detecting.

9. The method of claim 8, further including:
    effecting the relative translation of the cells along the translation path, wherein effecting the relative translation of the cells comprises applying at least one of a gravitational force, a centrifugal force, an electrokinetic force, a magnetic force, a hydraulic force, or a capillary force.

10. The method of claim 9, wherein effecting the relative translation of the cells comprises applying an electrokinetic force or a magnetic force.

11. The method of claim 10, wherein at least one force is an electrokinetic force.

12. The method of claim 11, wherein the electrokinetic force comprises electrophoresis.

13. The method of claim 12, wherein the electrophoresis is effected by a direct current applied to a first electrode and a second electrode, wherein the first electrode is located toward a first end of the translation path and the second electrode is located toward a second end of the translation path.

14. The method of claim 8 wherein said trapping electrical field is an alternating electric field and a time-vs.-field strength profile of the alternating electric field is rectangular.

15. The method of claim 8 wherein said trapping electrical field is an alternating electric field and the time-averaged integrated field strength of the alternating electric field taken over one complete cycle is zero.

16. The method of claim 8 wherein said trapping electrical field is an alternating electric field and the frequency of the alternating electric field is between about 10 Hz and 100 MHz.

17. The method of claim 16 wherein said trapping electrical field is an alternating electric field and the frequency of the alternating electric field is between about 1 KHz and 100 KHz.

18. The method of claim 8 wherein said trapping electrical field is an alternating electric field and the maximum field strength of the alternating electric field is between 100 V/cm and 100,000 V/cm.

19. The method of claim 18 wherein said trapping electrical field is an alternating electric field and the maximum field strength of the alternating electric field is between 1,000 V/cm and 20,000 V/cm.

20. The method of claim 8, wherein said trapping electrical field is an alternating electric field and the alternating electric field is spatially non-uniform.

21. A device for manipulating a plurality of cells, comprising:
   (a) a translation channel;
   (b) processing means disposed for communication with said device, said processing means being operable to control generation of a translational electrical field lengthwise along at least a portion of said translation channel and a trapping electrical field transverse to said translational electrical field, with said translational and trapping electrical fields crossing one another at an intersection defining a concentration zone;
   (c) a detector positioned to detect cells in the concentration zone, wherein the processing means is disposed for operable communication with the detector, and wherein the processing means is configured to alter at least one of the translational electric field and the trapping electric field in response to data received from the detector; and
   (d) an away of support-bound binding complements located in the concentration zone.

22. The device of claim 21, wherein the binding complements are selected from antibodies and receptor ligands.

23. The device of claim 21, wherein the detector is configured to detect each location in the array.

24. A device for manipulating a plurality of cells, comprising:
   (a) a translation channel;
   (b) processing means disposed for communication with said device, said processing means being operable to control generation of a translational electrical field lengthwise along at least a portion of said translation channel and a trapping electrical field transverse to said translational electrical field, with said translational and trapping electrical fields crossing one another at an intersection defining a concentration zone;
   (c) a detector positioned to detect cells in the concentration zone, wherein the processing means is disposed for operable communication with the detector, and wherein the processing means is configured to alter at least one of the translational electric field and/or the trapping electric field in response to data received from the detector; and
   (d) a frit located in the concentration zone, wherein the frit is made of an insulating matrix.

25. The device of claim 24 wherein an alternating current electrical conductivity of the insulating matrix is less than an alternating current electrical conductivity of a fluid medium located in pores of the frit.

26. The device of claim 25 wherein the alternating current electrical conductivity of the insulating matrix is at least 3 times less than that of the fluid medium.

27. The device of claim 26 wherein the alternating current electrical conductivity of the insulating matrix is between about 10 and 1000 times less than that of the fluid medium.

* * * * *

UNITED STATES PATENT AND TRADEMARK OFFICE
CERTIFICATE OF CORRECTION

| | | |
|---|---|---|
| PATENT NO. | : 7,704,363 B2 | Page 1 of 1 |
| APPLICATION NO. | : 11/288664 | |
| DATED | : April 27, 2010 | |
| INVENTOR(S) | : Bryning et al. | |

It is certified that error appears in the above-identified patent and that said Letters Patent is hereby corrected as shown below:

In Claim 21, Column 18, line 7, "away" should read --array--.

Signed and Sealed this

Second Day of November, 2010

David J. Kappos
*Director of the United States Patent and Trademark Office*